(12) United States Patent
Schibli et al.

(10) Patent No.: US 10,514,044 B2
(45) Date of Patent: Dec. 24, 2019

(54) PUMP HOUSING OF TWO DIFFERENT SINTERABLE MATERIALS

(71) Applicant: HERAEUS DEUTSCHLAND GMBH & CO. KG, Hanau (DE)

(72) Inventors: Stefan Schibli, Frankfurt (DE); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 341 days.

(21) Appl. No.: 14/900,509

(22) PCT Filed: Jun. 20, 2014

(86) PCT No.: PCT/EP2014/001684
§ 371 (c)(1),
(2) Date: Dec. 21, 2015

(87) PCT Pub. No.: WO2014/202225
PCT Pub. Date: Dec. 24, 2014

(65) Prior Publication Data
US 2016/0369813 A1 Dec. 22, 2016

(30) Foreign Application Priority Data
Jun. 21, 2013 (DE) .......................... 10 2013 211 848

(51) Int. Cl.
*A61M 1/10* (2006.01)
*F04D 29/52* (2006.01)
(Continued)

(52) U.S. Cl.
CPC ......... *F04D 29/528* (2013.01); *A61M 1/1012* (2014.02); *B22F 1/0059* (2013.01);
(Continued)

(58) Field of Classification Search
CPC .. A61M 1/101; A61M 1/1012; A61M 1/1015; A61M 1/1031; A61M 1/122;
(Continued)

(56) References Cited

U.S. PATENT DOCUMENTS 3,608,088 A * 9/1971 Dorman et al. ...... F04D 13/026
128/899
3,932,069 A 1/1976 Giardini et al.
(Continued)

FOREIGN PATENT DOCUMENTS

| CN | 1491323 | 4/2004 |
|---|---|---|
| CN | 1609455 | 4/2005 |

(Continued)

OTHER PUBLICATIONS

Search Report for International Application No. PCT/EP2014/001684 dated Oct. 24, 2014 (2 pgs.).
(Continued)

*Primary Examiner* — Justin D Seabe
*Assistant Examiner* — Adam W Brown
(74) *Attorney, Agent, or Firm* — Dicke, Billig & Czaja, PLLC

(57) ABSTRACT

One aspect of the invention relates to a pump device, comprising i. an impeller; ii. a pump housing which at least partly surrounds an interior region, having an inlet and an outlet, wherein the impeller is located within the interior region of the pump housing; wherein the pump housing comprises at least one first subregion and at least one further subregion; wherein the first subregion comprises a ceramic, wherein the further subregion comprises a metal, wherein at least one part of the first subregion and at least one part of the further subregion are connected to one another. One aspect of the invention further relates to a housing which comprises the features described for the pump housing.

(Continued)

One aspect of the invention also relates to a method for producing a pump housing.

19 Claims, 5 Drawing Sheets

(51) Int. Cl.
| | |
|---|---|
| F04D 3/00 | (2006.01) |
| F04D 29/02 | (2006.01) |
| B22F 1/00 | (2006.01) |
| B22F 3/00 | (2006.01) |
| B22F 3/16 | (2006.01) |
| B22F 7/00 | (2006.01) |
| B22F 7/06 | (2006.01) |
| B28B 1/24 | (2006.01) |
| C04B 37/02 | (2006.01) |
| C22C 32/00 | (2006.01) |
| F04D 29/18 | (2006.01) |
| A61M 1/12 | (2006.01) |

(52) U.S. Cl.
  CPC .............. *B22F 3/004* (2013.01); *B22F 3/16* (2013.01); *B22F 7/008* (2013.01); *B22F 7/06* (2013.01); *B28B 1/24* (2013.01); *C04B 37/021* (2013.01); *C22C 32/0021* (2013.01); *F04D 3/00* (2013.01); *F04D 29/026* (2013.01); *F04D 29/181* (2013.01); *A61M 1/122* (2014.02); *B22F 2301/25* (2013.01); *B22F 2302/253* (2013.01); *B22F 2304/10* (2013.01); *B22F 2998/10* (2013.01); *C04B 2237/343* (2013.01); *C04B 2237/408* (2013.01); *F05B 2240/142* (2013.01); *F05B 2240/30* (2013.01); *F05B 2280/10304* (2013.01); *F05B 2280/2004* (2013.01)

(58) Field of Classification Search
  CPC .......... B22F 1/0059; B22F 3/004; B22F 3/16; B22F 5/10; B22F 7/008; B22F 7/06; B22F 2301/25; B22F 2302/253; B22F 2304/10; B22F 2998/10; B28B 1/24; C04B 37/021; C04B 2237/343; C04B 2237/408; C22C 29/00; C22C 32/00; C22C 32/0021; F04D 3/00; F04D 13/024; F04D 13/0606; F04D 29/026; F04D 29/181; F04D 29/528; F05B 2240/142; F05B 2240/30; F05B 2280/103; F05B 2280/10304; F05B 2280/2004; F05B 2280/20041; F05B 2280/20043; F05D 2230/20; F05D 2230/40; F05D 2300/10; F05D 2300/133; F05D 2300/17; F05D 2300/20; F05D 2300/21; F05D 2300/507
  See application file for complete search history.

(56) References Cited

U.S. PATENT DOCUMENTS

| | | | |
|---|---|---|---|
| 4,603,062 A | | 7/1986 | Ecer |
| 4,806,080 A | | 2/1989 | Mizobuchi et al. |
| 5,112,200 A | | 5/1992 | Isaacson et al. |
| 5,370,509 A | | 12/1994 | Golding et al. |
| 5,470,208 A | | 11/1995 | Kletschka |
| 5,641,276 A | | 6/1997 | Heidelberg et al. |
| 5,822,839 A | | 10/1998 | Ghosh et al. |
| 5,840,070 A | | 11/1998 | Wampler |
| 5,990,588 A | | 11/1999 | Kliman et al. |
| 6,048,363 A | * | 4/2000 | Nagyszalanczy ... A61M 1/1086 415/900 |
| 6,053,705 A | * | 4/2000 | Schob ............... A61M 1/101 417/356 |
| 6,058,593 A | | 5/2000 | Siess |
| 6,158,984 A | | 12/2000 | Cao et al. |
| 6,227,817 B1 | * | 5/2001 | Paden ............... F04D 13/0646 417/356 |
| 6,234,772 B1 | * | 5/2001 | Wampler ............. A61M 1/101 415/900 |
| 6,466,209 B1 | | 10/2002 | Bantum |
| 6,499,209 B1 | | 12/2002 | Landin et al. |
| 6,663,362 B1 | | 12/2003 | Lentz et al. |
| 6,717,311 B2 | | 4/2004 | Locke |
| 7,229,258 B2 | | 6/2007 | Wood et al. |
| 8,007,254 B2 | | 8/2011 | LaRose et al. |
| 8,641,594 B2 | | 2/2014 | LaRose et al. |
| 8,821,365 B2 | | 9/2014 | Ozaki et al. |
| 8,864,643 B2 | * | 10/2014 | Reichenbach ............ A61F 2/07 285/315 |
| 9,850,906 B2 | | 12/2017 | Ozaki et al. |
| 2004/0062664 A1 | | 4/2004 | Weigold et al. |
| 2005/0279847 A1 | | 12/2005 | Kim |
| 2006/0127253 A1 | | 6/2006 | Ekberg et al. |
| 2007/0156006 A1 | | 7/2007 | Smith et al. |
| 2009/0022610 A1 | | 1/2009 | Materne et al. |
| 2012/0029265 A1 | | 2/2012 | LaRose et al. |
| 2012/0091832 A1 | | 4/2012 | Soderberg |
| 2012/0098371 A1 | | 4/2012 | Pinneo et al. |
| 2013/0096364 A1 | | 4/2013 | Reichenbach et al. |
| 2016/0369805 A1 | | 12/2016 | Keitel et al. |
| 2016/0369814 A1 | | 12/2016 | Schibli et al. |
| 2017/0102001 A1 | | 4/2017 | Schibli et al. |

FOREIGN PATENT DOCUMENTS

| | | |
|---|---|---|
| CN | 102387881 | 3/2012 |
| DE | 29723409 | 10/1998 |
| DE | 29907332 | 10/1999 |
| DE | 19956380 | 1/2001 |
| DE | 10108810 | 8/2002 |
| DE | 102006008423 | 8/2007 |
| DE | 10164898 | 9/2010 |
| DE | 112011102347 | 5/2013 |
| DE | 112011102354 | 5/2013 |
| EP | 2236229 | 10/2010 |
| JP | 2010-279490 | 12/2010 |
| WO | 9811650 | 3/1998 |
| WO | 0064030 | 10/2000 |
| WO | 2010050114 | 5/2010 |
| WO | 2010119267 | 10/2010 |
| WO | 2012132850 | 10/2012 |
| WO | 2014202225 | 12/2014 |
| WO | 2014202226 | 12/2014 |
| WO | 2014202227 | 12/2014 |

OTHER PUBLICATIONS

Translation of the Written Opinion of the International Searching Authority for International Application No. PCT/EP2014/001684 dated Oct. 24, 2014 (6 pgs.).
Office Action dated Apr. 5, 2019 in parallel U.S. Appl. No. 15/128,921.
International Preliminary Report on Patentability for International Application No. PCT/EP2015/056137 dated Oct. 6, 2016 (20 pgs).
International Search Report and Written Opinion for International Application No. PCT/EP2015/056137 dated Sep. 2, 2015 (21 pgs).
Office Action dated Jan. 17, 2018 in parallel U.S. Appl. No. 14/900,513.
Final Office Action dated Aug. 8, 2018 in parallel U.S. Appl. No. 14/900,513.
Office Action dated Dec. 20, 2018 in parallel U.S. Appl. No. 14/900,513.
Final Office Action dated May 30, 2019 in parallel U.S. Appl. No. 14/900,513.
Office Action dated Apr. 5, 2018 in parallel U.S. Appl. No. 14/900,515.
Final Office Action dated Nov. 10, 2018 in parallel U.S. Appl. No. 14/900,515.

(56) References Cited

OTHER PUBLICATIONS

Office Action dated Jun. 3, 2019 in parallel U.S. Appl. No. 14/900,515.
International Search Report and Written Opinion for International Application No. PCT/EP2014/001686 dated Mar. 12, 2014 (13 pages).
International Search Report and Written Opinion for International Application No. PCT/EP2014/001685 dated Oct. 24, 2010 (7 pgs.).
Polyurethanes and Medical Applications, American Chemistry Council, Retrieved on Mar. 26, 2019. Retrieved from the Internet: URL: https://polyurethane.americanchemistry.com/Polyurethanes-and-Medical-Applications, year 2019.
Molecular Weight of Aluminum Oxide, ConvertUnits.com (retrieved on Feb. 20, 2019). Retrieved from the Internet: URL: www.convertunits.com/molarmass/Aluminum+Oxide, year 2019.
Aluminum Oxide (Ai2O3) Balls, RGPBALLS S.r.l. 2019 (retrived on Mar. 14, 2019). Retrieved from the Internet: URL: www.rgpballs.com/en/aluminum-oxide-al2o3-balls/, year 2019.
Ashby, et al. Materials and Design: The Art and Science of Material Selection in Product Design, p. 218 (online), Second Edition, Elsevier 2002 (retrieved on Mar. 4, 2019). Retrieved from the Internet: URL: https://books.google.com/books?isbn=0080949401, year 2002.
Magnetic Permeability, Dura Magentics, Inc. Aug. 5, 2015 Retrieved on Mar. 25, 2019. Retrieved from the Internet: URL httpps:///www.duramag.com/techtalk/tech-briefs/magnetic-permeability-why-are-some-materials-attracted-by-a-magnet-and-others-are-not, year 2015.
Office Action dated Aug. 20, 2019 in parallel application U.S. Appl. No. 15/128,921.

\* cited by examiner

PUMP HOUSING OF TWO DIFFERENT SINTERABLE MATERIALS

CROSS REFERENCE TO RELATED APPLICATION

This Utility Patent Application claims the benefit of the filing date of German Application No. DE 10 2013 211 848.1, filed Jun. 21, 2013, and International Application No. PCT/EP2014/001684, filed Jun. 20, 2014, both of which are herein incorporated by reference.

BACKGROUND

One aspect of the invention relates to a pump device, comprising i. an impeller; ii. a pump housing which at least partly surrounds an interior region, having an inlet and an outlet, wherein the impeller is located within the interior region of the pump housing; wherein the pump housing comprises at least one first subregion and at least one further subregion; wherein the first subregion comprises a ceramic, wherein the further subregion comprises a metal, wherein at least one part of the first subregion and at least one part of the further subregion are connected to one another. One aspect of the invention further relates to a housing which comprises the features described for the pump housing.

One aspect of the invention also relates to a method for producing a pump housing, comprising the steps: a. providing a first material; b. providing a further material; c. forming a pump housing precursor, wherein a first subregion of the pump housing is formed from the first material and wherein a further subregion of the pump housing is formed from the further material; and d. treating the pump housing precursor at a temperature of at least 300° C.

Pump devices having rotors or impellers are known. Some pump devices have, as conveying route for a fluid to be conveyed, a pump housing in the form of a pipe. This often contains an impeller which is, for example, driven by a motor situated outside of the conveying route via a drive shaft. The pump housing is fastened to the pump device via one or more mounting elements. This type of retention can involve various disadvantages. Firstly, an additional work step is required in order to attach the mounting. This increases the production costs and is resource-inefficient. Furthermore, the connection between the pump housing and the mounting is not without tension owing to the production process or owing to the connecting means used, for example screws or rivets. This is because materials different to those for the pump housing are usually selected for the mountings and/or connecting means. Because of these tensions, the connections of the mounting to the pump housing deteriorate over time. Furthermore, especially in the case of very small pumps, it is extremely important for the pumps to be produced in a space-saving manner. This applies in particular to pumps which are to be implanted into a body. A space-saving construction is more difficult to realize for pumps having a multiplicity of individual parts than for a pump having a smaller number of individual parts.

In general, it is an object of the present invention to at least partly overcome the disadvantages arising from the prior art.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

Figure 1:
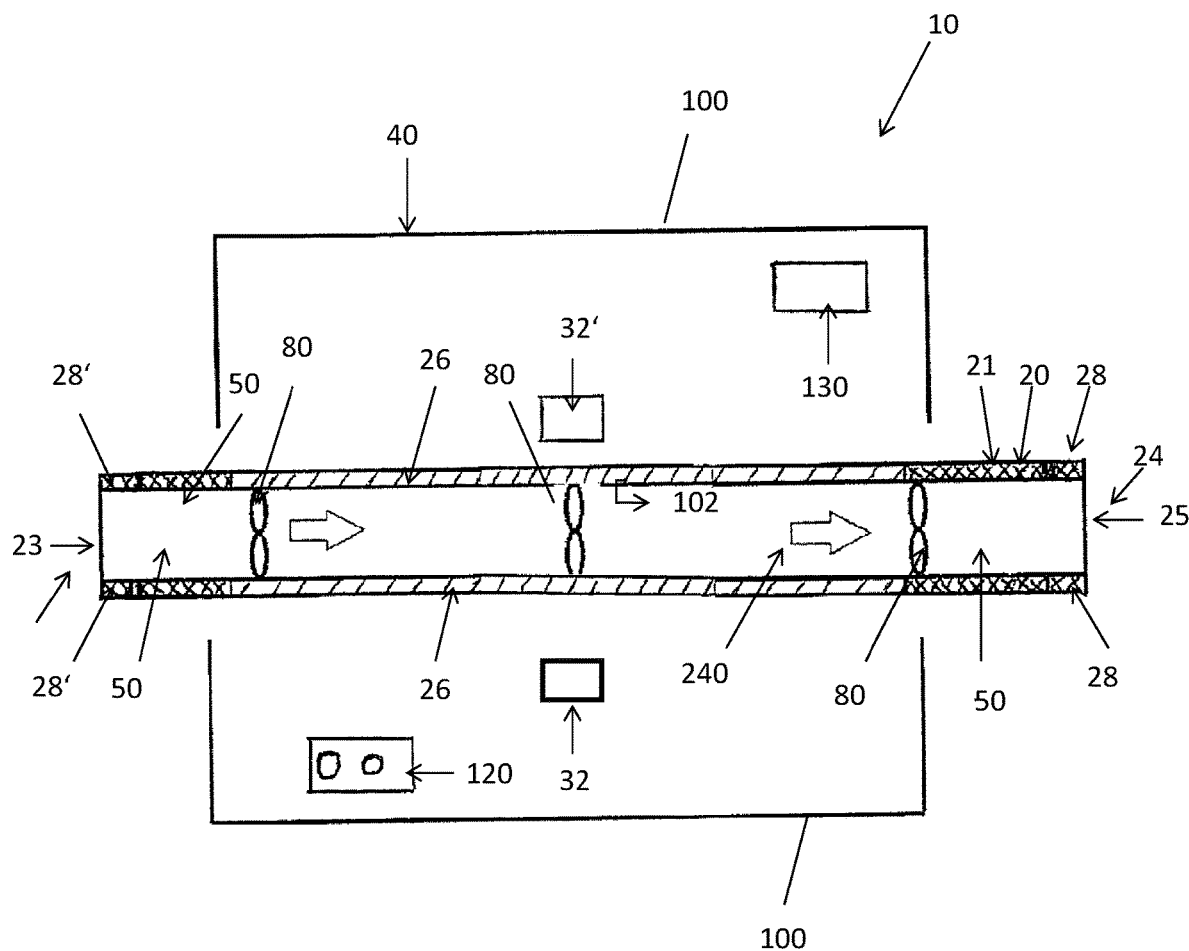
FIG. 1 illustrates a diagram of a pump device according to one embodiment of the invention.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

It is a further object of one embodiment to provide a pump device, the materials of which are as biocompatible as possible, as easily processable as possible, as corrosion-resistant as possible, and as permanently connectable to one another as possible.

It is a further object of one embodiment to provide a pump device which is designed to be as space-saving as possible.

Furthermore, it is an object of one embodiment to provide a pump device being as tension-free as possible, more particularly having a housing or pump housing being as tension-free as possible, and to provide in particular a passage from the pump housing to the remaining part of the pump device being as tension-free as possible.

In addition, it is an object of one embodiment to provide a pump device which has, during use, an abrasion of the movable parts and the mountings thereof as low as possible.

Furthermore, it is an object of one embodiment to provide a pump housing for a pump device which is integratable in an as simple and as space-saving manner as possible into other components, for example a component housing of the pump device.

Furthermore, it is an object of one embodiment to provide a pump housing for a pump device which can be connected in a hermetically sealed manner to a component housing of the pump device.

Furthermore, it is an object of one embodiment to provide a housing or pump housing which is as free from internal and/or external tensions as possible.

Furthermore, it is an object of one embodiment to provide a method which makes it possible to produce a pump housing in a manner being as cost-saving and time-saving manner as possible.

Furthermore, it is an object of one embodiment to provide a component housing which is designed to be as space-saving as possible.

It is a further object of one embodiment to provide a housing which can be connected in a hermetically sealed manner to other components.

A first object of one embodiment of the present invention is a pump device, comprising:
 i. an impeller;
 ii. a pump housing which at least partly surrounds an interior region, having an inlet and an outlet,
  wherein the impeller is located within the interior region of the pump housing;
  wherein the pump housing comprises at least one first subregion and at least one further subregion;
   wherein the first subregion comprises a ceramic to an extent of at least 61% by weight, preferably to an extent of at least 70% by weight, or preferably to an extent of at least 90% by weight, based on the total mass of the first subregion,
   wherein the further subregion comprises a metal content within a range from 40 to 90% by weight, based on the total mass of the further subregion, a metal,
   wherein at least one part of the first subregion and at least one part of the further subregion are connected to one another.

The pump device according to one embodiment of the invention is preferably suitable for introduction into the body of a human or of an animal. The pump device according to one embodiment of the invention is further preferably designed to convey body fluids such as blood, serum, plasma, interstitial fluid, saliva or urine. In particular, preference is given to introducing the pump device according to one embodiment of the invention into the blood circulation of a human or animal in order to convey blood. The introduction of the pump device according to one embodiment of the invention can, for example, involve an implantation into the body, a placement onto the body, or a connection to the body.

The pump housing of the pump device according to one embodiment of the invention can have any shape which a person skilled in the art would select for use in a pump device. The pump housing preferably has at least one wall of the pump housing, referred to hereinafter also as pump housing wall. The at least one wall of the pump housing surrounds the interior region of the pump housing. The pump housing has at least two ends, with at least one inlet being arranged at one end and at least one outlet being arranged at the other end. The interior region of the pump housing is, apart from at the inlet and outlet of the pump housing, completely surrounded by the wall. The pump housing can extend to some extent beyond the interior region of the pump housing. Preferably, the pump housing ends at the inlet or outlet.

The side of the pump housing that faces away from the interior region is referred to as the exterior of the pump housing. The pump housing preferably has an elongated shape. In terms of the shape thereof, the pump housing is defined by a longitudinal extent and at least one transverse section. A transverse section of the pump housing is always determined in a plane which is perpendicular to the pump housing wall. If the pump housing wall is curved in the longitudinal extent, a transverse section is determined perpendicularly to the tangent at one point on the pump housing wall. The extent of the pump housing in the pump direction is considered as the longitudinal extent. The shortest, imaginary connection between inlet and outlet within the pump housing is always applicable. The pump housing wall, also referred to as wall, extends in the direction of the longitudinal extent of the pump housing. The at least one wall can have one or more wall surfaces. If the pump housing has more than one wall surface, these are connected to one another via corners at which the wall surfaces converge. The wall, and preferably also the wall surfaces, of the pump housing preferably run parallel to the longitudinal extent of the pump housing. Part of the pump housing wall can extend beyond the interior region of the pump housing. Preferably, the pump housing wall extends across the entire interior region of the pump housing. If the pump housing is tubular, the inlet and the outlet are situated at the first end and at the opposing end, respectively, of the pump housing. At least one part of the pump housing wall preferably ends at the ends of the pump housing. The part of the pump housing which protrudes beyond the interior region into the surroundings is referred to as pump housing tongue. In a preferred design of the pump device according to one embodiment of the invention, the pump housing has a first opening to the interior region at the first end, i. e. the inlet, and a further opening to the interior region at the further end, i. e. the outlet. Via the inlet and outlet, the pump housing is connected in a fluid-guiding manner to the surroundings thereof. The openings at the ends of the pump housing allow a flow-through of a fluid through the interior region of the pump housing. The fluid is, for example, a gas, a liquid, such as blood, or a mixture thereof. Preferably, the first opening serves as supply line of the fluid to be conveyed into the interior region of the pump housing and the further opening serves as discharge line of the fluid to be conveyed. The pump housing can have further openings, for example in the wall of the pump housing. Said further openings can be used for the additional supply of fluid or, on the other side, for the branched discharge of fluid. If the pump device according to one embodiment of the invention is implanted into a body in order, for example, to support the blood circulation and to thus relieve the heart, the pump device according to one embodiment of the invention is connected via lines to blood vessels of the body.

The pump housing comprises at least one transverse section which is preferably selected from the group consisting of circular, rectangular or polyangular or ellipsoidal. Preferably, the pump housing has an elongated shape in at least one first segment. Furthermore, the pump housing can comprise at least one further segment, the shape of which deviates from the first segment of the pump housing.

Preferably, the total length of the pump housing is 1.5 to 10 times, preferably 2 to 9 times, or preferably 2.5 to 8.5 times longer than the diameter of the pump housing. The length of the pump housing is preferably determined along the outer wall of the pump housing in the pump direction. The pump housing preferably has a length within a range from 1 mm to 10 cm, or preferably within a range from 2 mm to 8 cm, or preferably within a range from 5 mm to 5 cm. The pump housing preferably has an inner diameter within a range from 0.1 to 50 mm, or preferably within a range from 0.5 to 30 mm, or preferably within a range from 1 to 20 mm.

The wall, more particularly the at least one wall surface of the pump housing, is preferably smooth. Smooth means that the wall of the pump housing has a roughness within a range from 0.025 to 4 Ra, or preferably within a range from 0.05 to 3 Ra, or preferably within a range from 0.07 to 1 Ra.

The pump housing comprises at least one first subregion and at least one further subregion. The first and the further subregion differ in the composition thereof. The at least one first subregion preferably has at least one, particularly preferably all, of the following properties:
- a heat resistance as high as possible;
- a pressure resistance as high as possible;
- a hardness as high as possible;
- a resistance to acids and bases as high as possible;
- a roughness as high as possible;
- a connectability to a metal or a metal-ceramic mixture (cermet) as tension-free as possible;
- a sinterability to a metal or a metal-ceramic mixture as good as possible;
- an electrical conductivity as low as possible;
- a magnetic permeability as low as possible.

The at least one further subregion preferably has at least one, particularly preferably all, of the following properties:
- a heat resistance as high as possible;
- a pressure resistance as high as possible;
- a resistance to acids and bases as high as possible;
- a roughness as low as possible;
- a sinterability to a ceramic material as good as possible;
- a connectability to a metal as good as possible;
- a weldability to a metal as good as possible.

When the two first and further subregions are brought together during the production of the pump housing, a pump housing which combines one or more of the listed properties for the at least one first subregion and the at least one further subregion can be obtained. At least one part of the at least one first subregion is connected to at least one part of the further subregion. The connection can be a direct connection of the two subregions or an indirect one. If the at least one first subregion and the at least one further subregion are directly connected to one another, the first subregion and the further subregion are connected to one another in a material-fitting manner.

There is a material-fitting connection when the material properties of the first subregion transition flowingly into the material properties of the further subregion. There is no sharp border between the two subregions. On the contrary, there is a transition zone in which the properties of the two subregions mix. Said transition zone is also referred to as the third subregion. In said third subregion, both the materials of the first subregion in part and the materials of the further subregion are present side by side and preferably form a mingling of the materials. Preferably, the materials of the two subregions form connections at the atomic or molecular level. Forces at the atomic or molecular level of the materials of the first and further subregions have an effect. Generally, such a material-fitting connection can only be released by destruction of the pump housing.

The at least one first subregion comprises a ceramic to an extent of at least 61% by weight, preferably to an extent of at least 70% by weight, or preferably to an extent of at least 90% by weight, based on the total mass of the first subregion. Preferably, the at least one first subregion comprises the ceramic within a range from 61 to 100% by weight, or preferably within a range from 70 to 100% by weight, or preferably within a range from 80 to 100% by weight, based on the total mass of the first subregion. Further preferably, the at least one first subregion comprises the ceramic to an extent of 100% by weight, based on the total mass of the first subregion. The at least one first subregion can comprise further materials. The further materials can be selected from the group consisting of water, an additive, a cermet or a mixture of at least two thereof.

The ceramic can be any ceramic which a person skilled in the art would select for the pump device according to one embodiment of the invention. The ceramic is preferably selected from the group consisting of an oxide ceramic, a silicate ceramic, a nonoxide ceramic or a mixture of at least two thereof.

The oxide ceramic is preferably selected from the group consisting of a metal oxide, a semimetal oxide or a mixture thereof. The metal of the metal oxide can be selected from the group consisting of aluminum, beryllium, barium, calcium, magnesium, sodium, potassium, iron, zirconium, titanium or a mixture of at least two thereof. The metal oxide is preferably selected from the group consisting of aluminum oxide ($Al_2O_3$), magnesium oxide (MgO), zirconium oxide ($ZrO_2$), yttrium oxide ($Y_2O_3$), aluminum titanate ($Al_2TiO_5$), a piezoceramic such as lead zirconate ($PbZrO_3$), lead titanate ($PbTiO_3$) and lead zirconate titanate (PZT) or a mixture of at least two thereof. The semimetal of the semimetal oxide is preferably selected from the group consisting of boron, silicon, arsenic, tellurium or a mixture of at least two thereof.

The silicate ceramic is preferably selected from the group consisting of a steatite ($Mg_3[Si_4O_{10}(OH)_2]$), cordierite ($Mg, Fe^{2+})_2[Al_2Si_4O_{18}]$), mullite ($Al_2Al_{2+2x}Si_{2-2x}O_{10-x}$ where x=oxygen vacancies per unit cell), feldspar ($Ba,Ca,Na,K, NH_4)(Al,B,Si)_4O_8$) or a mixture of at least two thereof.

The nonoxide ceramic can be selected from the group consisting of a carbide, a nitride or a mixture thereof. The carbide can be selected from the group consisting of silicon carbide (SiC), boron carbide ($B_4C$), titanium carbide (TiC), tungsten carbide, cementite (Fe3C). The nitride can be selected from the group consisting of silicon nitride ($Si_3N_4$), aluminum nitride (AlN), titanium nitride (TiN), silicon aluminum oxynitride (SIALON) or a mixture of at least two thereof.

Within the context of one embodiment of the invention, "cermet" is understood to mean a composite material composed of one or more ceramic materials in at least one metal matrix or a composite material composed of one or more metal materials in at least one ceramic matrix. A cermet can be produced by, for example, using a mixture of at least one ceramic powder and at least one metal powder, which can, for example, be admixed with at least one binder and optionally at least one solvent. A selection for the ceramic constituents and the metal constituents of the cermet can be made up of those which have been specified for the first subregion.

The at least one first subregion and the at least one further subregion can be arranged in different ways within the pump housing. Preferably, at least one surface of the at least one further subregion points toward the exterior of the pump housing and at least one surface of the at least one first subregion points toward the interior region. The at least one first subregion or the at least one further subregion can form the entire wall thickness in a transverse section of the pump housing. Alternatively, part of the wall thickness in a transverse section can comprise the first subregion and the other part of said wall thickness can comprise at least one further subregion. Preferably, the at least one first subregion and the at least one further subregion are designed as segments of the pump housing which extend consecutively along the longitudinal extent of the pump housing. If the pump housing has a third subregion, this preferably extends through the complete wall thickness of the pump housing at this point.

Figure 3A:
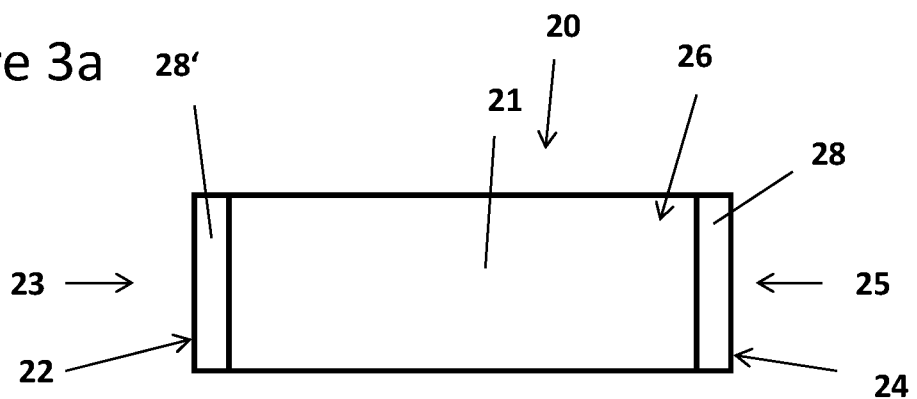
FIGS. 3a-c illustrate a diagram of a pump housing according to one embodiment of the invention having a first and a further subregion arranged directly adjacently to one another.
Figure 3B:
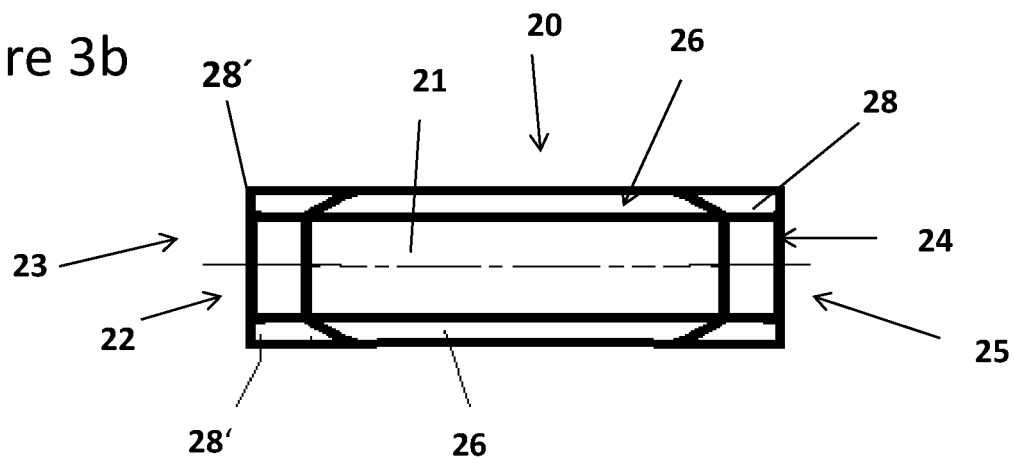
Figure 3C:
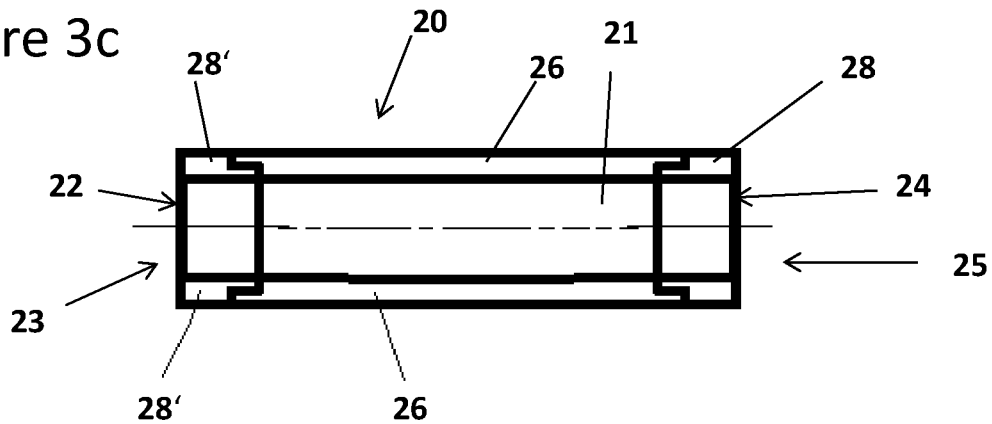

Any transition from one subregion to another subregion can be arranged at a right angle or at an angle other than 90° with respect to a transverse section of the pump housing. Furthermore, any transition can also be irregular, i.e., in the transverse section, no imaginary straight line can be placed on the transition. Furthermore, any transition from one subregion to another subregion can, as an alternative or in addition to what has been described above, be arranged at a right angle or at an angle other than 90° with respect to a longitudinal section through a wall of the pump housing. Furthermore, any transition can also be irregular, i.e., in the longitudinal section, no imaginary straight line can be placed on the transition. Furthermore, preference is given to combinations of the aforementioned configurations of a transition in the transverse section and in the longitudinal section. Examples in relation thereto are shown in FIGS. 3a to 3c.

In a preferred design of the pump housing, the at least one first, one further or one third subregion can at least partly extend diagonally in relation to the longitudinal extent of the pump housing. Owing to this, the pump housing can have transverse sections of the pump housing which have, along the wall thickness, both a first and a further subregion, or both a first and a third subregion. This is shown by way of example in FIG. 4b.

Moreover, the pump device according to one embodiment of the invention comprises a rotor in the form of the impeller. The impeller can have any shape which a person skilled in the art would select for this purpose.

The impeller preferably has a diameter within a range from 1 mm to 10 cm, preferably within a range from 3 mm to 5 cm, or preferably within a range from 5 mm to 3 cm. The impeller preferably has a thickness within a range from 0.1 to 50 mm, preferably within a range from 0.5 to 20 mm, or preferably within a range from 1 to 15 mm. The diameter of the impeller is preferably smaller than the diameter of the pump housing in the plane of the impeller. The diameter of the impeller is preferably within a range from 1 to 10%, or preferably within a range from 1.5 to 8%, or preferably within a range from 2 to 7%, based on the diameter of the pump housing in the plane of the impeller, smaller than the diameter of the pump housing.

The impeller preferably has at least two rotor blades, preferably at least three rotor blades, or preferably at least five rotor blades. Particularly preferably, the impeller has a rotor blade number within a range from 2 to 20, preferably within a range from 5 to 15, or preferably within a range from 8 to 13. The impeller preferably has a central rotation axis, around which the impeller can be rotated. The rotation axis is also referred to as axis of rotation. The at least two rotor blades are preferably arranged symmetrically around the rotation axis of the impeller. The impeller is preferably arranged within the interior region of the pump housing, with the axis of rotation of the impeller being parallel to the longitudinal extent of the wall of the pipe.

The impeller can be produced from any material which a person skilled in the art would select for use in the pump device according to one embodiment of the invention.

Preferably, the impeller has at least two regions: A first region at the center of the impeller around the axis of rotation. Said first region is also referred to as core region. A second region, also referrered to as rotor region. Said second region has at least two rotor blades which are suitable for conveying the fluid to be conveyed.

The impeller comprises at least one element having hard-magnetic properties. A hard-magnetic property means that a material receives a permanent magnetization as a consequence of exposure of said material in a magnetic field. The strength of a magnetizing field is selected depending on the composition of the element. The required considerations and calculations are familiar to a person skilled in the art. Preferably, the induction of the impeller is saturated during magnetization. After the magnetic field has dropped, the magnetization of the hard-magnetic material persists. Materials having hard-magnetic properties can be used as permanent magnets. The at least one element is preferably arranged on the impeller such that it moves the impeller when it is alternately attracted and repelled by two independent electric or magnetic fields. The impeller preferably comprises at least two elements having hard-magnetic properties. Furthermore, by means of at least one optional element, it is possible to control the impeller with respect to its radial, but also axial, alignment. Preferably, the elements having hard-magnetic properties are used to mount the impeller in a highly contact-free manner in the pump housing without any further auxiliary means, such as mountings or other fixings in the pump housing. This allows an operation that is especially low in abrasion and especially low in wear and tear.

The at least one element can, for example, be realized by at least one rotor blade which comprises a hard-magnetic material. Alternatively, a hard-magnetic element can be arranged on at least one rotor blade. Preferably, the hard-magnetic element is located in the core of the impeller. The at least one hard-magnetic element preferably comprises at least one magnetizable material, such as iron, cobalt, nickel, chromium dioxide or a mixture of at least two thereof. The at least one element can, for example, be arranged in the form of a coating composed of hard-magnetic material on at least one rotor blade or inside the impeller. Preferably, at least 50%, or preferably at least 70%, or preferably 100% of the rotor blades comprise a hard-magnetic material. Preferably, the element comprises a hard-magnetic metal to an extent of at least 10% by weight, or preferably to an extent of at least 20% by weight, or preferably to an extent of at least 30% by weight, based on the total mass of the element. Further preferably, the element comprises a cobalt-chromium alloy or a platinum-cobalt alloy, more particularly a platinum-cobalt alloy (PtCo23) having a proportion of cobalt of 23% by weight, based on the total mass of the alloy, within a range from 10 to 100% by weight, or preferably within a range from 20 to 100% by weight, or preferably within a range from 30 to 100% by weight, based on the total mass of the element.

The impeller can have in its core—the region around the rotation axis—a material different to that in or on the rotor blades. Alternatively, the impeller can comprise a uniform material in the core and the rotor blades. The material of the rotor blades can be flexible or inflexible. Preferably, the material of the core of the impeller or the material of the rotor blades of the impeller is selected in each case from the group consisting of a polymer, a metal, a ceramic or a combination or mixture of at least two thereof.

The polymer can be selected from the group consisting of a chitosan, a fibrin, a collagen, a caprolactone, a lactide, a glycolide, a dioxanone, a polyurethane, a polyimide, a polyamide, a polyester, a polymethyl methacrylate, a polyacrylate, a Teflon, a copolymer of at least two thereof or a mixture of at least two thereof.

The metal can be selected from the group consisting of iron (Fe), stainless steel, platinum (Pt), iridium (Ir), niobium (Nb), molybdenum (Mo), tungsten (W), titanium (Ti), cobalt (Co), chromium (Cr), a cobalt-chromium alloy, tantalum (Ta), vanadium (V) and zirconium (Zr) or a mixture of at least two thereof, with particular preference being given to titanium, niobium, molybdenum, cobalt, chromium, tantalum, zirconium, vanadium and the alloys thereof.

The ceramic can be selected from the group consisting of aluminum oxide ($Al_2O_3$), zirconium dioxide ($ZrO_2$), hydroxylapatite, tricalcium phosphate, glass-ceramic, aluminum oxide-reinforced zirconium oxide (ZTA), zirconium oxide-containing aluminum oxide (ZTA—Zirconia Toughened Aluminum—$Al_2O_3/ZrO_2$), yttrium-containing zirconium oxide (Y-TZP), aluminum nitride (AlN), titanium nitride (TiN), magnesium oxide (MgO), piezoceramic, barium (Zr, Ti) oxide, barium (Ce, Ti) oxide and sodium potassium niobate or a mixture of at least two thereof.

Further preferably, the impeller can be coated with a biocompatible material on its exterior, more particularly on the outer surface of the rotor blades. Suitable biocompatible materials will be described further below.

The impeller is preferably arranged within the interior region of the pump housing which is surrounded by the first subregion. The impeller is preferably arranged with its axis of rotation parallel to the longitudinal extent of the wall. Furthermore, the impeller can be aligned by a magnetic field within the pump housing. The impeller within the interior region of the pump housing is preferably aligned by magnetic fields of electric coils on the exterior of the pump housing. The coils preferably comprise an electrically conductive material. Preferably, the electrically conductive material of the coils is selected from the group consisting of iron (Fe), copper (Cu), gold (Au), silver (Ag), platinum (Pt), palladium (Pd), titanium (Ti), chromium (Cr), cobalt (Co), tungsten (W) or a mixture of at least two thereof. Further preferably, the electrically conductive material comprises copper (Cu). The pump device according to one embodiment of the invention preferably comprises at least two coils, preferably at least three coils, or preferably at least four coils. The coils are preferably arranged on the exterior of the pump housing, with the coils and the impeller preferably lying in one plane. They are then arranged on the exterior of the pump housing around the impeller.

In a preferred design of the pump device according to one embodiment of the invention, the pump housing comprises a pipe. Preferably, the pipe is straight. Alternatively, the pipe can have at least one bend. The pipe is preferably closed with the exception of an inlet and an outlet. This means that the pipe has no further openings apart from the two openings at the inlet and outlet. The dimensions, materials and designs preferably otherwise correspond to those of the above-described pump housing.

In a preferred design of the pump device according to one embodiment of the invention, there is at least one further subregion at the inlet or the outlet.

In another preferred design of the pump device according to one embodiment of the invention, there is one further subregion at both the inlet and the outlet.

In a preferred design of the pump device according to one embodiment of the invention, the pump housing has a volume within a range from 0.1 $cm^3$ to 10 $cm^3$, preferably within a range from 0.2 to 9 $cm^3$, or preferably within a range from 0.5 to 5 $cm^3$. Preferably, the dimensions such as length, diameter and wall thickness of the pump housing are as already specified above. The volume of the pump housing is defined by the inner space surrounded by the pump housing. The wall of the pump housing preferably has a thickness within a range from 0.1 to 5 mm, or preferably within a range from 0.3 to 4 mm, or preferably within a range from 0.4 to 3 mm. Hereinafter, wall thickness will be mentioned in this connection. At the inner surface of the pump housing, the wall thicknesses can vary in at least one of the first or the further subregions. An increase in wall thickness at at least one point of the pump housing can serve the purpose of keeping the impeller at its position in the pump housing at least in one direction.

In a preferred design of the pump device according to one embodiment of the invention, the ceramic of the at least one first subregion is selected from the group consisting of aluminum oxide ($Al_2O_3$), zirconium dioxide ($ZrO_2$), a zirconium oxide containing an aluminum oxide (ATZ—Aluminum toughened Zirconia), an aluminum oxide containing a zirconium oxide (ZTA—Zirconia Toughened Aluminum), a zirconium oxide containing an yttrium (Y-TZP), aluminum nitride (AlN), titanium nitride (TiN), magnesium oxide (MgO), a piezoceramic, barium (Zr, Ti) oxide, barium (Ce, Ti) oxide and sodium potassium niobate or a mixture of at least two thereof.

The at least one further subregion of the pump housing comprises a metal content within a range from 40 to 90% by weight, preferably within a range from 45 to 85% by weight, or within a range from 50 to 80% by weight, based on the total mass of the further subregion.

In a preferred design of the pump device according to one embodiment of the invention, the metal of the further subregion is selected from the group consisting of platinum (Pt), iron (Fe), stainless steel (AISI 304, AISI 316 L), iridium (Ir), niobium (Nb), molybdenum (Mo), tungsten (W), titanium (Ti), cobalt (Co), chromium (Cr), a cobalt-chromium alloy, tantalum (Ta) and zirconium (Zr) or a mixture of at least two thereof. Preferably, the metal is selected from the group consisting of titanium, niobium, molybdenum, cobalt, chromium, tantalum and the alloys thereof or a mixture of at least two thereof.

Furthermore, the at least one further subregion can comprise further materials. The further material can, as already described for the first subregion, be selected from the group consisting of an additive, a ceramic, a cermet or a mixture of at least two thereof.

The ceramic of the further subregion can be any ceramic which a person skilled in the art would select for a pump device. The ceramic is preferably selected from the group consisting of an oxide ceramic, a silicate ceramic, a nonoxide ceramic or a mixture of at least two thereof. The ceramic of the at least one further subregion can be selected from the same group as the ceramics listed for the first subregion. Preferably, the at least one further subregion has the same ceramic as the at least one further subregion. The further subregion comprises the ceramic preferably within a range from 1 to 60% by weight, or preferably within a range from 5 to 55% by weight, or preferably within a range from 10 to 45% by weight, based on the total mass of the further subregion.

Furthermore, the at least one further subregion can comprise an additive, as has been described for the first subregion. The additive preferably comprises a material selected from the group consisting of water, a dispersant, a binder or a mixture of at least two thereof. All further properties and specified quantities relating to the additives can be gathered from the details relating to the first subregion. The sum of all constituents of the further subregion is always 100% by weight.

A selection for the ceramic constituents and the metal constituents of the cermet can be composed of those which have been specified for the at least one further subregion.

The pump housing preferably comprises at least one first subregion and at least one further subregion. The pump housing can have multiple first subregions and multiple further subregions. Preferably, the pump housing has a number of first subregions within a range from 1 to 10, preferably from 1 to 8, or preferably from 1 to 5. Preferably, the pump housing has a number of further subregions within a range from 1 to 10, preferably from 2 to 8, or preferably from 2 to 5. Preferably, the pump housing comprises a first subregion and two further subregions. The at least first and the at least further subregion can be the same size or alternatively have different sizes. The at least one first subregion and the at least one further subregion preferably extend across the entire thickness of the pump housing wall. The thickness of the first and the further subregion are preferably identical and correspond to the wall thickness as specified above for the pump housing wall. The at least one first subregion preferably has a width, based on the longitudinal extent of the pump housing, within a range from 1 to 100 mm, preferably within a range from 2 to 70 mm, or preferably within a range from 3 to 50 mm. The at least one further subregion preferably has a width, based on the longitudinal extent of the pump housing, within a range from 0.5 to 80 mm, preferably within a range from 1 to 60 mm, or preferably within a range from 2 to 20 mm. If the pump housing has more than one first and/or more than one further subregion, the multiple first and/or multiple further subregions are preferably equally wide. Alternatively, differently wide first and differently wide further subregions can alternate.

In a preferred embodiment of the pump device according to one embodiment of the invention, the pump housing comprises at each of its two ends an identically sized further subregion. These are connected via a first subregion. Preferably, the two further subregions have a width within a range from 1 to 10 mm, or preferably within a range from 2 to 8 mm, or preferably within a range from 2.5 to 6 mm. Furthermore, the one first subregion preferably has a width from 5 to 40 mm, preferably within a range from 10 to 30 mm, or preferably within a range from 15 to 25 mm.

In a further preferred embodiment of the pump device according to one embodiment of the invention, the pump housing comprises at each of its two ends a further subregion, the two further subregions being separated by a first subregion. Preferably, the two further subregions have a width within a range from 3 to 30 mm, or preferably within a range from 5 to 20 mm, or preferably within a range from 7 to 15 mm. Further preferably, the one first subregion has a width from 0.5 to 10 mm, or preferably within a range from 1 to 8 mm, or preferably within a range from 2 to 6 mm. The two further subregions, one at the inlet and one at the outlet, can have identical or different widths, diameters and wall thicknesses. Preferably, the pump housing at the inlet and/or outlet has at least one different inner diameter compared with the remaining inner diameter of the pump housing. The different inner diameter can be achieved either by differently thick wall thicknesses or by a different arrangement or geometry of the further subregions at the first subregion.

Furthermore, the at least one first subregion can comprise a metal. The metal can be any metal which a person skilled in the art would select for the manufacture of the pump housing.

In a preferred design of the pump device according to one embodiment of the invention, the at least one first subregion comprises less than 10% by weight, preferably less than 5% by weight, or preferably less than 3% by weight, based on the total mass of the first subregion, of metal. The sum of all constituents of the first subregion is always 100% by weight.

The metal of the first subregion is preferably selected from the group consisting of platinum (Pt), iron (Fe), stainless steel (AISI 304, AISI 316 L), iridium (Ir), niobium (Nb), molybdenum (Mo), tungsten (W), titanium (Ti), cobalt (Co), chromium (Cr), a cobalt-chromium alloy, tantalum (Ta), and zirconium (Zr) or a mixture of at least two thereof. Preferably, the metal is selected from the group consisting of titanium, niobium, molybdenum, cobalt, chromium, tantalum and the alloys thereof or a mixture of at least two thereof. Preferably, the first subregion has the same metal as the further subregion.

In a preferred design of the pump device according to one embodiment of the invention, the at least one first subregion and the at least one further subregion are connected to one another by at least one third subregion. Preferably, each first subregion is connected to each further subregion via a third subregion.

In a preferred design of the pump device according to one embodiment of the invention, the at least one third subregion has a metal content between the metal content of the first subregion and the metal content of the further subregion. Owing to the production process of the pump housing, the third subregion can be situated between the at least one first and the at least one further subregion. Alternatively, during the production process, a third subregion can have been introduced at least between a first and a further subregion. The third subregion preferably comprises a ceramic and a metal. The ceramic is preferably selected from the ceramics listed for the first subregion. The metal is preferably selected from the metals listed for the further subregion. The third subregion comprises the ceramic preferably within a range from 10 to 90% by weight, or preferably within a range from 20 to 80% by weight or preferably within a range from 30 to 70% by weight, based on the total mass of the third subregion. The third subregion comprises the metal preferably within a range from 10 to 89% by weight, or preferably within a range from 20 to 80% by weight or preferably within a range from 30 to 70% by weight, based on the total mass of the third subregion. The sum of all constituents of the third subregion is always 100% by weight. The third subregion preferably has a metal content which is yielded by the mean of the metal content of the first subregion and of the further subregion. The third subregion can serve the purpose of reducing or minimizing tensions between the different materials of the first and of the further subregion. Preferably, the connection between the first and the third subregion is material-fitting. Further preferably, the connection between the second and the third subregion is likewise material-fitting. Preferably, the first, the further and the third subregion have the same ceramic or the same ceramics and the same metal or the same metals.

In a preferred design of the pump device according to one embodiment of the invention, the pump device is at least partly surrounded by a component housing, with at least one part of the at least one further subregion of the pump device being connected to the component housing. The connection of the component housing to at least one part of the further subregion of the pump housing preferably leads to a closed space between the component housing and the pump housing. Preferably, the interior of the component housing of the pump device is hermetically closed with respect to the surroundings. The medically implantable pump device proposed here according to one embodiment of the invention can in particular be inserted into a body of a human or animal user, more particularly of a patient. An implantable pump device is generally exposed to a fluid of a body tissue of the body. Therefore, it is generally important that body fluid does not penetrate the medically implantable device, and that the fluids do not escape from the medically implantable device. In order ensure this, the component housing of the medically implantable device, and thus also the component housing and the pump housing of the pump device according to one embodiment of the invention, should have very complete impermeability, particularly against body fluids.

The pump device according to one embodiment of the invention, more particularly connections of component housing to pump housing, is preferably hermetically sealed. Thus, the interior space of the pump device is sealed off in a hermetically sealed manner with respect to the exterior space. In the context of one embodiment of the invention, the term "hermetically sealed" means that, during intended use, no moisture and/or gases can penetrate the hermetically sealed connection within a customary period of 5 years. A physical variable in relation to determining the seal tightness of a connection or of a component is the leak rate. Seal tightnesses can be determined by leak tests. Appropriate leak tests are carried out using helium leak testers and/or mass spectrometers and are specified in the standard Mil-STD-883G, method 1014. In this connection, the maximum permitted helium leak rate is defined depending on the internal volume of the device to be tested. In accordance with the methods specified in MIL-STD-883G, method 1014, in section 3.1, and in consideration of the volumes and cavities of the devices to be tested that occur when applying the present invention, the maximum permitted helium leak rate for the pump housing according to one embodiment of the invention is $10^{-7}$ atm*cm$^3$/sec or less. This means that the device to be tested (for example, the component housing and/or the pump device according to one embodiment of the invention or the component housing with the connected pump housing) has a helium leak rate of less than $1\times10^{-7}$ atm*cm$^3$/sec or less. In a particularly advantageous embodiment, the helium leak rate is less than $1\times10^{-8}$ atm*cm$^3$/sec, more particularly less than $1\times10^{-9}$ atm*cm$^3$/sec. For the purposes of standardization, the aforementioned helium leak rates can also be converted to the equivalent standard air leak rate. The equivalent standard air leak rate and the conversion are defined in the standard ISO 3530.

The pump device according to one embodiment of the invention preferably has, in addition to the impeller, the pump housing having a first and a further subregion, preferably a component housing in which further components of the pump device can be situated. The further components of the pump device are preferably selected from the group consisting of a battery, a coil, a control unit, a vessel connection unit or a combination of at least two thereof.

In a preferred design of the pump device according to one embodiment of the invention, the component housing comprises titanium to an extent of at least 30% by weight, preferably at least 50% by weight, or preferably at least 80% by weight, based in each case on the total mass of the component housing. Further preferably, the component housing comprises titanium to an extent of at least 99% by weight, based on the total mass of the component housing. Furthermore, the component housing can preferably comprise at least one other metal. The other metal can be selected from the same group as the metal of the further subregion. The other metal is preferably selected from the group consisting of Fe, Al, V, Sn, Co, Cr, CoCr, Nb, stainless steel, Mb, TiNb or a mixture of at least two thereof. The component housing can comprise the further metal preferably within a range from 1 to 70% by weight, or preferably within a range from 5 to 50% by weight, or preferably within a range from 10 to 20% by weight. The sum of all constituents of the component housing is always 100% by weight. Suitable titanium qualities are specified in ASTM 6265-05: 2011, for example grades 1 to 6.

In a preferred design of the pump device according to one embodiment of the invention, the wall of the pump housing has a magnetic permeability of less than 2μ, preferably less than 1.9μ, or preferably less than 1.8μ. The magnetic permeability is determined in accordance with the standard ASTM 773-01:2009.

In a preferred design of the pump device according to one embodiment of the invention, the surface of the at least one first subregion which faces the interior region of the pump housing has a Vickers hardness of at least 330 HV, preferably at least 350 HV, or preferably at least 370 HV. Preferably, the entire at least one first subregion has a hardness within the specified ranges. At least the surface of the at least one further subregion likewise has a Vickers hardness of at least 330 HV, preferably at least 350 HV, or preferably at least 370 HV. The hardness is frequently not greater than 2000 HV, or preferably not greater than 1500 HV. Preferably, the hardness of at least the surface of the at least one first subregion is within a range from 330 to 2000 HV, or preferably within a range from 350 to 1800 HV. Further preferably, at least the surface of the at least one first subregion has a hardness which is at least just as great as the hardness of the rotor surfaces of the impeller. Preferably, at least the surface of the at least one first subregion has a hardness which is greater by at least 20 HV, or preferably by at least 30 HV, or preferably by at least 40 HV than the Vickers hardness of the rotor surfaces of the impeller. Surface of the at least one subregion, of the at least one further subregion and of the impeller is understood to mean the material layer close to the surface within a range from 0.01 to 2.5 mm, preferably within a range from 0.05 to 1.0 mm, or preferably within a range from 0.1 to 0.5 mm, perpendicular in each case to the surface.

In a preferred design of the pump device according to one embodiment of the invention, at least the outer surfaces of the component housing and the surface facing the interior region of the pump housing are biocompatible. This is especially preferred when the pump device for implantation into a living body, such as, for example, that of a human or animal. The biocompatibility is determined and assessed in accordance with the standard ISO 10993-4:2002.

Generally, the surfaces facing the interior region of the pump housing and the outer surfaces of the component housing come into contact with the body fluid of a living body after implantation of the pump device according to one embodiment of the invention into said living body. The biocompatibility of the surfaces coming into contact with body fluid contributes to the body suffering no damage upon contact with said surfaces.

One aspect of the present invention further provides a method for producing a pump housing for a pump device, comprising the steps:
 a. providing a first material;
 b. providing a further material;
 c. forming a pump housing precursor, wherein a first subregion of the pump housing is formed from the first material and wherein a further subregion of the pump housing is formed from the further material;
 d. treating the pump housing precursor at a temperature of at least 300° C.

Providing the first material in step a. and the further material in step b. can be done in any desired manner which a person skilled in the art would select for this purpose.

Forming of the pump housing precursor can be done in any desired manner which a person skilled in the art would select for the purpose of forming a first subregion and a further subregion. In a preferred design of the method, step c. comprises a shaping process, preferably selected from the group consisting of a lithographic process, an injection molding process, a machining process, an extrusion process or a combination of at least two thereof.

In a lithographic process, various layers of one or more materials are successively shaped. The lithographic process preferably corresponds to a layer-by-layer screen printing process. In the screen printing process, a screen, consisting of a very dimensionally stable material, such as wood; metal, preferably steel; a ceramic or a plastic, having a selected mesh opening is arranged on the object to receive an overlay or over the object to receive an overlay. The printing composition used for application or overlaying, for example in the form of a paste or a powder, is applied to said screen via a nozzle or from a container and pressed through the mesh openings of the screen using a doctor blade. Owing to a pattern in the screen, it is possible to apply at different sites varying amounts of the printing composition used for application or overlaying. For instance, owing to the geometry and arrangement of the mesh openings, it is possible either to apply a uniform film of the printing composition used for overlaying or to alternate regions having little or no printing composition used for application with regions having much printing composition used for application. Preferably, a uniform film of the printing composition used for overlaying is transferred to the surface. The screen mesh openings can also be partly closed by appropriately applied materials (copying layers, screen printing templates), and so the printing composition is transferred to the surface to be coated only in defined regions having open mesh openings in order to thus obtain, for example, a defined structure such as a pattern. Furthermore, instead of screens, it is also possible to use thin films having defined openings (stencil) for transfer of the printing composition. By repetition of this procedure with the same material or else different materials, it is possible to obtain 3D structures.

In one embodiment of the process, the first subregion can already be present as fired ceramic. Preferably, the first subregion is present as a pipe having a length of 2 cm with an inner diameter of 9 mm. At least one layer of the further material is then preferably applied by screen printing to the ceramic at at least one end of the first subregion. The screen printing procedure is repeated until a 5 mm layer of further subregion is applied to the end of the first subregion. Alternatively, all subregions can be produced successively by screen printing.

Injection molding is a shaping process for at least one material for obtaining a shaped solid body. A person skilled in the art is aware from the prior art of different injection molding methods and of tools and conditions used for injection molding. Injection molding can be selected from the group consisting of a multicomponent injection molding process, a powder injection molding process, an injection-compression molding process, an extrusion-injection molding process, a negative-pressure injection molding process or a combination of at least two thereof.

Machining can be combined with any other shaping process. Machining involves structuring a solid body through use of machining tools, such as a drill or a punch. During structuring, part of the material is removed. As a result, solid bodies can, for example, be shaped to give hollow bodies. For example, by means of machining, it is possible to shape a cavity into the pump housing precursor if the pump housing precursor is solid. However, machining can also be a processing step after the production of a pump housing or housing. In addition to machining, a polishing process can also take place following the production of the pump housing.

During forming of the pump housing precursor in step c., a first material for forming a first subregion is contacted with a further material for forming the further subregion. The contacting procedure preferably takes place in the form of an injection molding process, in which there is successive injection firstly of the further material into a mold composed of metal and subsequently of the first material. The proportions in the first and the further material preferably correspond to the proportions in the first and the further subregion, as have been described above in connection with the first subject matter, the pump device according to one embodiment of the invention. Furthermore, the first and the further material can contain additives. Preferably, the pump housing precursor already has the shape of the pump housing after the contacting procedure. Preferably, the two materials form a continuous shape. The contacting procedure can additionally comprise one or more further steps. For instance, a third material, which preferably a composition such as the third subregion of the above-described pump device according to one embodiment of the invention, can be introduced into the pump housing precursor between the first material and the further material.

The additive selected can be any substance which a person skilled in the art would select as supplement for the first material. The additive is preferably selected from the group consisting of water, a dispersant, a binder or a mixture of at least two thereof.

The dispersant preferably comprises at least one organic substance. The organic substance preferably has at least one functional group. The functional group can be a hydrophobic or a hydrophilic functional group. The functional group can be selected from the group consisting of an ammonium group, a carbon/late group, a sulfate group, a sulfonate group, an alcohol group, a polyalcohol group, an ether group or a mixture of at least two thereof. The dispersant has functional groups preferably within a range from 1 to 100, or preferably within a range from 2 to 50, or preferably within a range from 2 to 30. Preferred dispersants are available under the trade names DISPERBYK® 60 from Byk-Chemie GmbH and DOLAPIX CE 64 from Zschimmer & Schwarz GmbH & Co KG.

The binder is preferably selected from the group consisting of a methylcellulose, a thermoplastic polymer, a thermoset polymer and a wax or a mixture of at least two thereof.

The methylcellulose is preferably selected from the group consisting of hydroxypropylmethylcellulose (HPMC), hydroxyethylmethylcellulose (HEMC), ethylmethylcellulose (EMC) or a mixture thereof. The methylcellulose preferably comprises hydroxypropylmethylcellulose (HPMC). Further preferably, the methylcellulose comprises hydroxypropylmethylcellulose within a range from 80 to 100% by weight, or preferably within a range from 90 to 100% by weight, or preferably within a range from 95 to 100% by weight, based on the total mass of methylcellulose. Preferably, the methylcellulose has a proportion of —OCH$_3$ groups within a range from 20 to 40% by weight, or preferably within a range from 23 to 37% by weight, or preferably within a range from 25 to 35% by weight, based on the total mass of methylcellulose. Further preferably, the methylcellulose has a proportion of —OC$_3$H$_6$OH groups within a range from 1 to 12% by weight, or preferably within a range from 3 to 9% by weight, or preferably within a range from 4 to 8% by weight, based on the total mass of methylcellulose.

The thermoplastic polymer can be selected from the group consisting of acrylonitrile-butadiene-styrene (ABS), polyamides (PA), polylactate (PLA), polymethyl methacrylate (PMMA), polycarbonate (PC), polyethylene terephthalate (PET), polyethylene (PE), polypropylene (PP), polystyrene (PS), polyether ether ketone (PEEK) and polyvinyl chloride (PVC) or a mixture of at least two thereof. The thermoset polymer can be selected from the group consisting of an aminoplast, an epoxy resin, a phenolic resin, a polyester resin or a mixture of at least two thereof. Waxes are hydrocarbon compounds which melt above 40° C. without decomposition. These can also include polyesters, paraffins, polyethylenes or copolymers of at least two thereof.

The first material comprises at least one of the aforementioned additives preferably within a range from 0.1 to 10% by weight, or preferably within a range from 0.2 to 8% by weight, or preferably within a range from 0.5 to 5% by weight, based on the total mass of the first material.

The further material comprises at least one of the aforementioned additives preferably in a quantity within a range from 0.1 to 5% by weight, or preferably within a range from 0.2 to 2% by weight, or preferably within a range from 0.3 to 1% by weight, based in each case on the total weight of the further material.

Treating the pump housing precursor in step d. can be done in any desired manner which a person skilled in the art would select for the purpose of heating the pump housing precursor to at least 300° C. Preferably, at least part of the treatment of the pump housing precursor takes place at a temperature within a range from 300 to 2500° C., or within a range from 500 to 2000° C., or within a range from 700 to 1800° C. During the treatment of the pump housing precursor at elevated temperature, preferably at least part of the binder escapes. Various temperature profiles are possible during the treatment in step d. of the pump housing precursor from step c. The pump housing precursor can, for example, be treated in an oxidative atmosphere, a reductive atmosphere or under a protective atmosphere. An oxidative atmosphere can, for example, contain oxygen, such as air or an oxygen/air mixture. A reductive atmosphere can, for example, contain hydrogen. A protective atmosphere preferably comprises neither oxygen nor hydrogen. Examples of protective atmospheres are nitrogen, helium, argon, krypton or mixtures thereof. The selection of the atmosphere may be dependent on the materials to be treated. A person skilled in the art knows the appropriate selection of atmosphere for the materials mentioned. It is also preferably possible to successively select combinations of different atmospheres for various time periods.

The pump housing precursor can be treated either in one step or preferably in more than one step. Preferably, the pump housing precursor is treated in a first substep of step d. to a temperature within a range from 301 to 600° C., or preferably within a range from 350 to 550° C., or preferably within a range from 400 to 500° C. Said first substep of treatment step d. can take place over a period within a range from 0.1 to 100 h, preferably within a range from 1 to 50 h, or preferably within a range from 2 to 20 h. Said substep can take place either by introduction of the pump housing precursor from step c. into a preheated atmosphere or by slow stepwise or continuously increased heating of the pump housing precursor. Preferably, the treatment in the first substep of step d. of the pump housing precursor is performed in one step at a temperature within a range from 301 to 600° C.

In a second substep of the treatment from step d., which preferably follows the first substep, the pump housing precursor is preferably heated to a temperature within a range from 800 to 2500° C., or preferably within a range from 1000 to 2000° C., or preferably within a range from 1100 to 1800° C. Said substep, too, can take place either by introduction of the pump housing precursor from the first substep of step d. into a preheated atmosphere or by slow stepwise or continuously increased heating of the pump housing precursor. Preferably, the treatment in the second substep of step d. of the pump housing precursor is performed in one step to a temperature within a range from 800 to 2500° C. The treatment of the pump housing precursor in the second substep is performed over a period within a range from 0.1 to 20 h, preferably within a range from 1 to 12 h, or preferably within a range from 2 to 5 h.

The shape of the pump housing after the production process is preferably continuous. This means that the pump housing does not have any further openings or outlets, or other recesses, apart from the outlet and the inlet. Preferably, the pump housing has a straight outer surface. At the inner surface of the pump housing, the wall thicknesses can vary in at least one of the first or the further subregions. An increase in wall thickness at at least one point of the pump housing can serve the purpose of keeping the impeller at its position in the pump housing at least in one direction. In this connection, thickening of the wall thickness can take place either during the production process or after said process. In addition or as an alternative, the pump housing can have constrictions.

One aspect of the present invention further provides a method for producing a pump housing for a pump device, comprising the steps:
a) providing a first material;
b) providing a further material;
c) forming a pump housing precursor, wherein firstly a further subregion of the pump housing is formed from the further material and then a first subregion of the pump housing is formed from the first material and wherein a second further subregion of the pump housing is formed from the further material;
d) treating the pump housing precursor at a temperature of at least 300° C.

Providing the first material in step a) and the further material in step b) can be carried out as before in the above-described method for producing a pump housing.

Forming of the pump housing precursor in step c) can be carried out in any desired manner which a person skilled in the art would select for the purpose of forming a first subregion and a further subregion, with observance of the specified order. Details concerning individual substeps have already been specified in the above-described method.

A pump device according to one embodiment of the invention is obtainable by insertion of an impeller into a pump housing, arrangement of electromagnets with coils around the pump housing, and establishment of a circuit with inclusion of a control device and a power source, for example a battery. Preferably, the pump device according to one embodiment of the invention is surrounded by a component housing and the further subregions of the pump housing are connected to the component housing in a material-fitting manner. This can, for example, be carried out by means of a solder connection along the contact point of pump housing and component housing.

In a preferred design of the method for producing a pump housing, step c. comprises a shaping process preferably selected from the group consisting of a lithographic process, an injection molding process, a machining process, an extrusion process or a combination of at least two thereof. Details concerning the various shaping processes have been described for the above-described method for producing a pump housing precursor. The properties and parameters mentioned therein also apply to this production process.

During forming of the pump housing precursor in step c., a first material for forming a first subregion is contacted with a further material for forming the further subregion. The contacting procedure preferably takes place in the form of an injection molding process, in which there is successive injection firstly of the further material into a mold composed of metal and subsequently of the first material. The composition of the first and the further material preferably correspond to the compositions of the first or further subregions, as have been described above in connection with the first subject matter, the pump device according to one embodiment of the invention. Preferably, the pump housing precursor already has the shape of the pump housing after the contacting procedure. Preferably, the two materials form a continuous shape. Furthermore, a further part of the further material is again contacted with the first material. This yields a pump housing precursor which has along its tubular shape firstly a first further subregion of the further material, neighbored by a first subregion of the first material. Said first subregion is in turn neighbored by a second further subregion of further material. The extents and compositions of the subregions correspond to those specified in relation to the pump device according to one embodiment of the invention. The contacting procedure can additionally comprise one or more further steps. For instance, a third material, which preferably a composition such as the third subregion of the above-described pump device according to one embodiment of the invention, can be introduced into the pump housing precursor between the first material and the further material.

Treating the pump housing precursor in step d. can be done in any desired manner which a person skilled in the art would select for the purpose of heating the pump housing precursor to at least 300° C. Preferably, at least part of the treatment of the pump housing precursor takes place at a temperature within a range from 300 to 2500° C., or within a range from 500 to 2000° C., or within a range from 700 to 1800° C. During the treatment of the pump housing precursor at elevated temperature, preferably at least part of the binder escapes. Various temperature profiles are possible during the treatment in step d. of the pump housing precursor from step c. The pump housing precursor can, for example, be treated in an oxidative atmosphere, a reductive atmosphere or under a protective atmosphere. An oxidative atmosphere can, for example, contain oxygen, such as air or an oxygen/air mixture. A reductive atmosphere can, for example, contain hydrogen. A protective atmosphere preferably comprises neither oxygen nor hydrogen. Examples of protective atmospheres are nitrogen, helium, argon, krypton or mixtures thereof. It is also preferably possible to successively select combinations of different atmospheres for various time periods.

The pump housing precursor can be treated either in one step or preferably in more than one step. Preferably, the pump housing precursor is treated in a first substep of step d. to a temperature within a range from 301 to 600° C., or preferably within a range from 350 to 550° C., or preferably within a range from 400 to 500° C. Said first substep of treatment step d. can take place over a period within a range from 0.1 to 100 h, preferably within a range from 1 to 50 h, or preferably within a range from 2 to 20 h. Said substep can take place either by introduction of the pump housing precursor from step c. into a preheated atmosphere or by slow stepwise or continuously increased heating of the pump housing precursor. Preferably, the treatment in the first substep of step d. of the pump housing precursor is performed in one step at a temperature within a range from 301 to 600° C.

In a second substep of the treatment from step d., which preferably follows the first substep, the pump housing precursor is preferably heated to a temperature within a range from 800 to 2500° C., or preferably within a range from 1000 to 2000° C., or preferably within a range from 1100 to 1800° C. Said substep, too, can take place either by introduction of the pump housing precursor from the first substep of step d. into a preheated atmosphere or by slow stepwise or continuously increased heating of the pump housing precursor. Preferably, the treatment in the second substep of step d. of the pump housing precursor is performed in one step to a temperature within a range from 800 to 2500° C. The treatment of the pump housing precursor in the second substep is performed over a period within a range from 0.1 to 20 h, preferably within a range from 1 to 12 h, or preferably within a range from 2 to 5 h. As stated above, the shape of the pump housing after the production process is preferably continuous.

One aspect of the present invention further provides a pump housing for a pump device obtainable by the above-described method according to the invention.

One aspect of the present invention further provides a housing which at least partly surrounds an interior region, having a first end and a second end,
  wherein the housing has at least one first subregion and at least one further subregion;
  wherein the first subregion comprises a ceramic to an extent of at least 61% by weight, based on the total mass of the first subregion,
  wherein the further subregion comprises a metal content within a range from 40 to 90% by weight, or preferably within a range from to 45 to 85% by weight, or preferably within a range from 50 to 80% by weight, based on the total mass of the further subregion,
  wherein at least one part of the first subregion and at least one part of the further subregion are connected to one another.

In terms of its shape, its composition and other design, the housing corresponds to the pump housing which has been described above in connection with the pump device according to one embodiment of the invention.

In a preferred design of the housing, a slidable element is located in the housing, at least in one part of the housing. Further preferred embodiments correspond to the above-described embodiments of the pump device according to one embodiment of the invention.

The slidable element can be selected from the group consisting of a ball, a cylinder, an air bubble or a combination of at least two thereof. The slidable element preferably has a shape which corresponds to the diameter of the pump housing. The material of the slidable element can be any which a person skilled in the art would use for this purpose. Preferably, the slidable element comprises a metal, a polymer, a ceramic or a mixture thereof. The metal or the polymer can be selected from a metal, a polymer or a ceramic as has been described for the first subregion for the pump housing. The slidable element can serve the purpose of, for example, becoming shifted in terms of its position in the housing by a change in the fluid stream in the housing. Upon a change in the position of the slidable element, it is possible to trigger a current flow in a coil and to record it by means of a current flow measurement.

One aspect of the present invention further provides a pump device comprising at least one above-described housing or a pump housing obtainable by an above-described method.

Measurement Methods

1. Determination of Vickers hardness (HV):

The test forces and materials were determined in accordance with the standard DIN EN ISO 6507, March 2006. The following test forces and exposure times were used: 1 kg, 15 seconds. The test temperature was 23° C.±1° C.

2. Determination of magnetic permeability: Magnetic permeability was determined in accordance with the standard ASTM 773-01:2009.

3. Determination of biocompatibility:

Biocompatibility is determined in accordance with the standard ISO 10993-4:2002.

4. Determination of hermetic connection:

Leak tests are carried out using helium leak testers and/or mass spectrometers. A standard measurement method is specified in the standard Mil-STD-883G, method 1014. In this connection, the maximum permitted helium leak rate is defined depending on the internal volume of the device to be tested. In accordance with the methods specified in MIL-STD-883G, method 1014, in section 3.1, and in consideration of the volumes and cavities of the devices to be tested that occur when applying the present invention, the maximum permitted helium leak rate for the pump housing according to the invention is $10^{-7}$ atm*cm$^3$/sec or less. This means that the device to be tested (for example, the component housing and/or the pump device or the component housing with the connected pump housing) has a helium leak rate of less than $1 \times 10^{-7}$ atm*cm$^3$/sec or less. For the purposes of comparison, the aforementioned helium leak rates can also be converted to the equivalent standard air leak rate. The equivalent standard air leak rate and the conversion are defined in the standard ISO 3530.

5. Determination of roughness:

Roughness is determined in accordance with the standard EN ISO 25178.

EXAMPLES

Example 1 for First Material

The first material contains 20 parts of aluminum oxide ($Al_2O_3$) available from CeramTech GmbH, having a particle size of $D_{90}=2$ µm, and one part of the binder METAWAX P-50 available from Zschimmer & Schwarz GmbH & Co. KG.

Example 2 for Further Material

The further material contains a mixture of 57% by weight of a platinum powder from Heraeus Precious Metals GmbH & Co. KG, having a particle size of $D_{50}=50$ µm, and 38% by weight of aluminum oxide ($Al_2O_3$) from CeramTech GmbH, having a particle size of $D_{90}=2$ µm, and 5% by weight of a binder METAWAX P-50 available from Zschimmer & Schwarz GmbH & Co.KG.

Example 3 for First Subregion

The first subregion contains, to an extent of 100% by weight, aluminum oxide ($Al_2O_3$) from CeramTech GmbH Example 4 for Further Subregion The further subregion contains, to an extent of 60% by weight, platinum and, to an extent of 40% by weight, aluminum oxide ($Al_2O_3$) from CeramTech GmbH.

Figure 5:
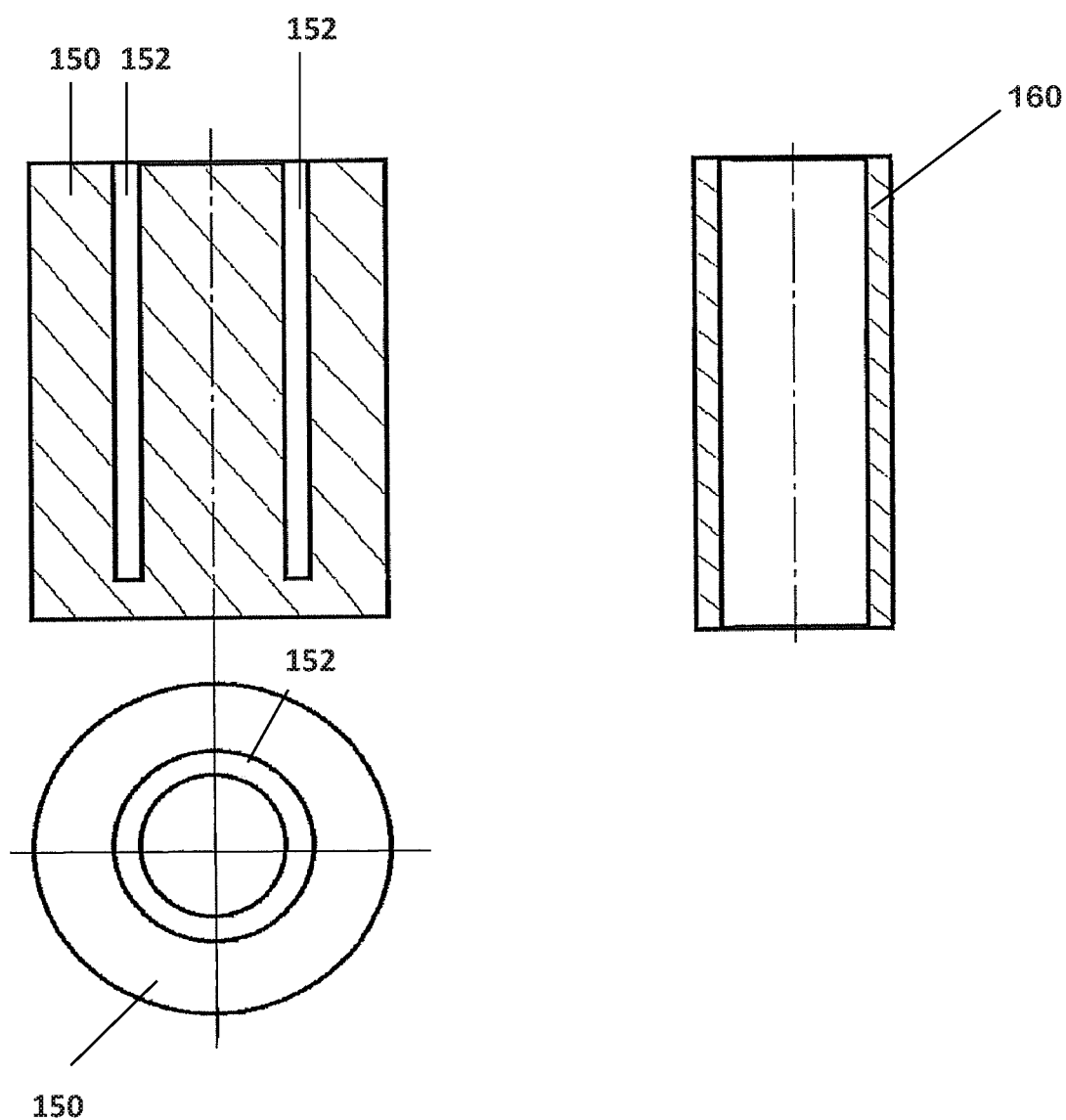
FIG. 5 illustrates a diagram of a compressing device for producing a pump housing precursor.

In accordance with the method according to one embodiment of the invention for the production of a pump housing, the first material from example 1 is firstly provided in a container. The further material from example 2 is likewise provided in a container. In an alternating sequence, the powders of the further material and of the first material are added to the mold, as shown in FIG. 5, and compressed using a punch. This yields a pump housing precursor which is firstly treated at a temperature of 400° C. and subsequently sintered at a temperature of 1700° C. in a furnace to give a pump housing.

FIG. 1 shows a diagram of a pump device 10 which has a pump housing 20, in the form of a pipe, and a component housing 40. The outer surfaces 100 of the component housing 40 come, especially for an implantable pump device 10, into contact with the body and are therefore preferably biocompatible. The pump housing 20 has a wall 21 which surrounds an interior region 50. The surface of the pump housing 20 that faces the interior region 50 is referred to as facing surface 102. The facing surface 102 comes into contact with the fluid and is therefore, especially for an implantable pump device 10, preferably biocompatible. The interior region 50 of the pump housing 20 contains at least one impeller 80; in this case, two impellers 80 are situated in the pump housing 20. The pump housing 20 has a first subregion 26 in the middle of the wall 21. At the first end 22, which simultaneously defines the inlet 22 by the opening 23, the wall 21 or the pump housing 20 has a first further subregion 28. Situated on the opposing side of the pump housing 20 is the further end 24, in the form of the outlet 24, comprising the further opening 25. By means of the impeller 80, it is possible to pump a fluid in pump direction 240 from the inlet 22 to the outlet 24. Situated between the component housing 40 and the pump housing are further components, such as a battery 120 and a control unit 130. Furthermore, two coils 32 and 32' are situated in the component housing 40.

Figure 2:
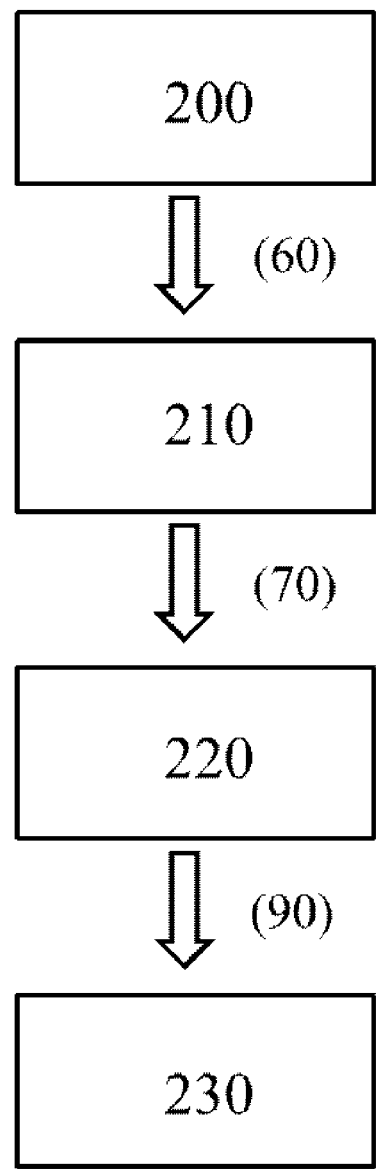
FIG. 2 illustrates a diagram of a method for producing a pump housing according to one embodiment of the invention.

FIG. 2 shows a diagram of the sequence of the method for producing a pump housing. In step a. or a) 200, a first material 60 is provided. The first material 60 is, for example, a mixture of at least two powders. The first material contains the composition from example 1, viz. 20 parts of aluminum oxide ($Al_2O_3$) having a particle size of $D_{90}=2$ µm and one part of a binder, in this case METAWAX P-50 available from Zschimmer & Schwarz GmbH & Co. KG.

In a step b. or b) 210, the further material 70 is provided, likewise preferably in a container, in the form of a mixture, corresponding to example 2, of 57% by weight of a platinum powder having a particle size of $D_{50}$=50 μm, and 38% by weight of aluminum oxide ($Al_2O_3$) having a particle size of $D_{90}$=2 μm, and 5% by weight of a binder, in this case METAWAX P-50 available from Zschimmer & Schwarz GmbH & Co. KG. The container can be a metal container having a screen outlet. Preferably, the powder particles have a round to oval extent. The specified particle size $D_{50}$ means that not more than 50% of the particles are greater than the specified diameter. The specified particle size $D_{90}$ means that not more than 90% of the particles are greater than the specified diameter. The particle size can be determined using various methods. Preferably, the particle size is determined using laser diffraction, light microscopy, optical single particle counting or a combination of at least two thereof. Further preferably, the determination of particle size and of particle size distribution is performed by means of transmission electron microscopy (TEM) on the basis of optical individual evaluation of images. Also, the particle size can be gathered from the product data sheet which is available from the raw material supplier and often enclosed with a shipment.

In a step c. or c) 220, a pump housing precursor 90 is formed from the first material 60 and the further material 70.

Steps c. or c) 200 are two alternatives which can be followed in the formation of the pump housing precursor 90; In the first alternative of step c., a further subregion 28 is firstly formed by the further material 70. In this case, using a Teflon doctor blade having the dimensions 10 mm*4 mm*2 mm and a doctor blade hardness of 50 shore, the further material 70 is pressed into a mold 150 composed of an aluminum oxide ceramic, as shown diagrammatically in FIG. 5. The further material 70 is filled into the mold 150 up to a fill level of 5 mm. Thereafter, the first material 60 is pressed into the mold 150 from FIG. 5. The first material 60 is filled up to a fill level of 25 mm. Using a stainless steel punch, the first and the further material 70 is compressed under a pressure from a 5 kg weight. In the pump housing precursor 90 thus formed, the first subregion 26 of the pump housing 20 of the first material 60 is consequently present beside the further subregion 28 of the pump housing 20.

In the alternative of step c), the procedure is exactly as described above for step c., with the difference that the first material 60 is filled only up to a fill level of 25 mm. Thereafter, a second further subregion of the pump housing precursor 90 is formed, by again filling a further material 70, as described above, into the mold 150 up to a fill level of 30 mm. This yields a pump housing precursor 90 which provides a sequence of a first further subregion 28, 28' beside a first subregion 26, 26' and a second further subregion 28, 28'. The thicknesses of the first further subregion 28', 28, of the first subregion 26, 26' and of the second further subregion 28, 28' are identical. By selecting the shape of the mold 150 into which the materials are added, it is possible to achieve differences in the wall thicknesses at least in parts of the subregions 26, 28, 30.

Subsequently, the pump housing precursor 90 is treated at a temperature of 400° C. in air. This treatment takes place in a heating furnace from Heraeus Holding GmbH for a period of 60 min. Directly after this treatment step, the pump housing precursor 90 is treated at a temperature of 1700° C. in the same furnace for 180 min, whereby the subregions 26, 28 sinter together an whereby a pump housing is formed.

The result is a pump housing in the form of a round pipe having an inner diameter of 9 mm. The wall thickness in all regions is 1 mm.

FIGS. 3a to 3c show three different ways of arranging multiple subregions in one pump housing 20 according to one embodiment of the invention. In its wall 21, the pump housing 20 comprises a first opening 23 at the inlet 22 and a further opening 25 at the outlet 24. In FIG. 3a, a first subregion 26 is arranged in the middle of the wall 21 of the pump housing 20. To the right and the left thereof, there is in each case a further subregion 28 and 28'. The two further subregions 28 and 28' are arranged parallel to one another and to the first subregion 26.

FIG. 3b likewise shows a pump housing 20 having a wall 21 and a first subregion 26 in the middle of the wall 21. Here too, a further subregion 28 and 28' is connected in each case to the inlet 22 and outlet 24. Unlike the pump housing 20 from FIG. 3a, the further subregions 28 and 28' are not arranged parallel to the first subregion 26 in the entire extent of the pump device; instead, they have segments of varying width across the extent of the pump housing 20. This results in a diagonal profile of the transition from the first subregion 26 to the further subregions 28, 28'.

FIG. 3c too shows a nonparallel transition from the further subregions 28, 28' to the first subregion 26. Here, the transition has an offset. Otherwise, the pump housing 20 from FIG. 3c is constructed like that from FIG. 3a.

Figure 4A:
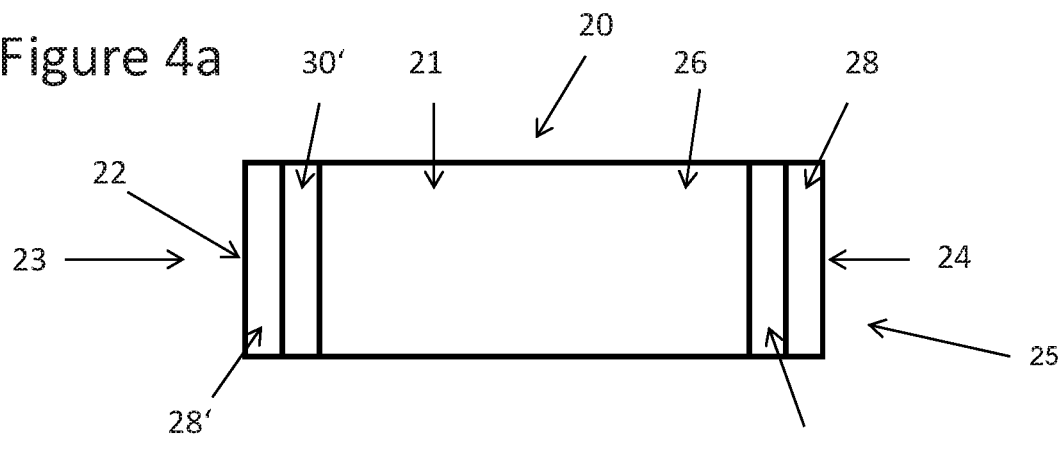
FIGS. 4a-c illustrate a diagram of a pump housing according to one embodiment of the invention having a first and a further subregion arranged separated by a third subregion.
Figure 4B:
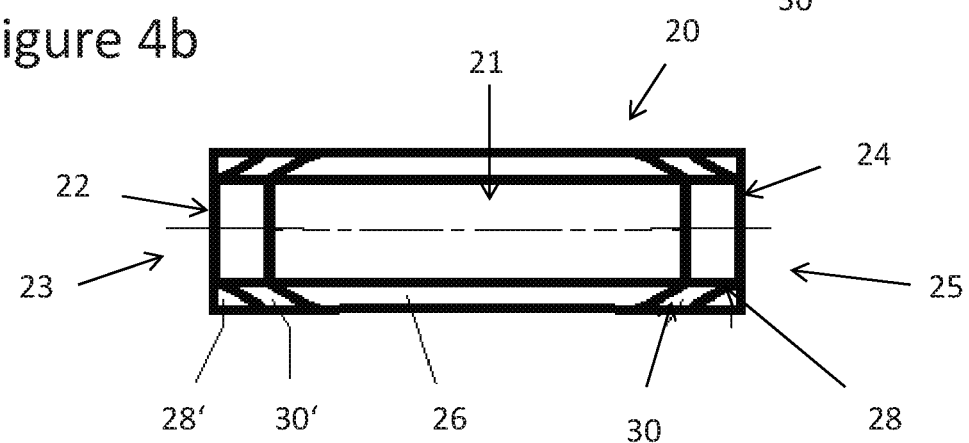
Figure 4C:
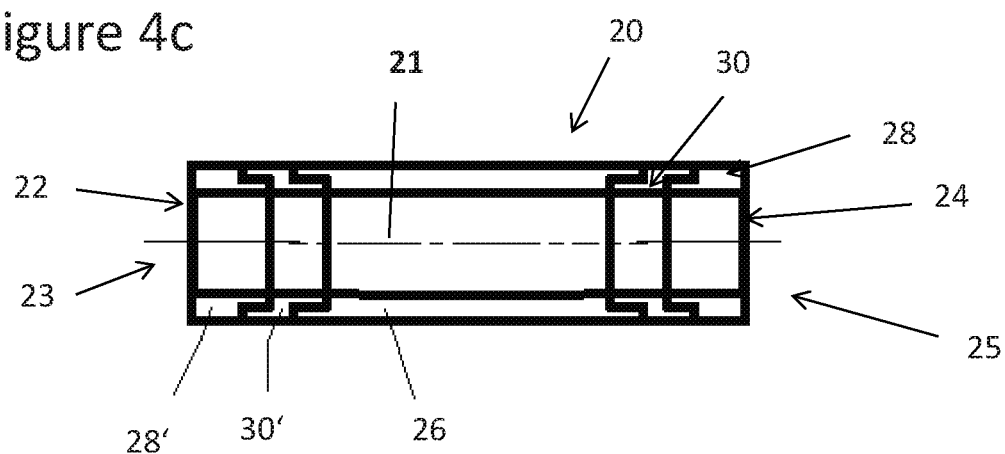

FIGS. 4a, 4b and 4c each show a similar structure of a pump housing 20 with respect to FIGS. 3a, 3b and 3c; however, a third subregion 30 and 30' are arranged here between, in each case, a first subregion 26 and the further subregion 28 and 28'. Otherwise, the structure of the pump housing from FIG. 4a corresponds to that of FIG. 3a, that of FIG. 4b to that from 3b, and the structure of the pump housing from FIG. 4c corresponds to that of the pump housing from FIG. 3c.

FIG. 5 shows a mold 150 which is made from a solid material, such as a ceramic or a stainless steel. A round recess 152 has been milled into the mold 150, which recess opens outward on one side of the mold 150. Through the opening, it is possible to fill material, which is for example pasty or powdery, into the mold 150 and to compress it using the punch 160, which fits exactly into the opening of the mold 150. In this way, it is possible to make a blank or a precursor for a pump housing 20 in the form of a pipe, as has already been described for the method in FIG. 2.

The invention claimed is:
1. A pump device comprising:
    a pump housing at least partly surrounding an interior region and having an inlet and an outlet; and
    an impeller located within the interior region of the pump housing;
    wherein the pump housing comprises at least one first subregion and at least two further subregions, a material of the first subregion being different than a material of the further subregions;
    wherein the first subregion comprises a ceramic to an extent of at least 61% by weight, based on the total mass of the first subregion;
    wherein the further subregions comprises a metal content within a range from 40 to 90% by weight, based on the total mass of the further subregions;
    wherein at least one part of the first subregion and at least one part of the further subregions are connected to one another; and wherein the at least one first subregion and the at least two further subregions alternate on an exterior circumference of the pump housing.

2. The pump device of claim 1, wherein the pump housing comprises a pipe.

3. The pump device of claim 1, wherein the at least two further subregions are positioned at the inlet or the outlet, or at both the inlet and the outlet.

4. The pump device of claim 1, wherein the ceramic of the at least one first subregion is selected from the group consisting of aluminum oxide ($Al_2O_3$), zirconium dioxide ($ZrO_2$), a zirconium oxide containing an aluminum oxide (ATZ), an aluminum oxide containing a zirconium oxide (ZTA), a zirconium oxide containing an yttrium (Y-TZP), aluminum nitride (AlN), titanium nitride (TiN), magnesium oxide (MgO), a piezoceramic, barium oxide and sodium potassium niobate or a mixture of at least two thereof.

5. The pump device of claim 1, wherein the metal of the at least one two further subregions is selected from the group consisting of platinum (Pt), iron (Fe), stainless steel, iridium (Ir), niobium (Nb), molybdenum (Mo), tungsten (W), titanium (Ti), cobalt (Co), chromium (Cr), a cobalt-chromium alloy, tantalum (Ta) and zirconium (Zr) or a mixture of at least two thereof.

6. The pump device of claim 1, wherein the at least one first subregion comprises less than 10% by weight of metal based on the total mass of the first subregion.

7. The pump device of claim 1, wherein the at least one first subregion and the at least two further subregions are connected to one another by at least one third subregion.

8. The pump device of claim 7, wherein the at least one third subregion has a metal content between the metal content of the first subregion and the metal content of the further subregions.

9. The pump device of claim 1, wherein the pump device is at least partly surrounded by a component housing, with at least one part of the at least two further subregions of the pump device being connected to the component housing.

10. The pump device of claim 9, wherein the component housing comprises at least 30% by weight of titanium based on the total mass of the component housing.

11. The pump device of claim 1, wherein the wall of the pump housing has a magnetic permeability of less than 2μ.

12. The pump device of claim 1, wherein the surface of the at least one first subregion that faces the interior region of the pump housing has a Vickers hardness of at least 330 HV.

13. The pump device of claim 1, wherein at least the outer surfaces of the component housing and the surface facing the interior region of the pump housing are biocompatible.

14. A method for producing a pump housing for a pump device, the method comprising:
providing a first material;
providing a further material that is different than the first material;
forming a pump housing precursor, wherein a first subregion of the pump housing is formed from the first material and wherein two further subregions of the pump housing are formed from the further material and wherein the first subregion and the two further subregions alternate on an exterior circumference of the pump housing; and
treating the pump housing precursor at a temperature of at least 300° C.

15. A method for producing a pump housing for a pump device, comprising the steps:
providing a first material;
providing a further material that is different than the first material;
forming a pump housing precursor, wherein firstly at least two further subregions of the pump housing are formed from the further material and then a first subregion of the pump housing is formed from the first material and wherein a second further subregion of the pump housing is formed from the further material, and wherein the first subregion and the two further subregions alternate on an exterior circumference of the pump housing; and
treating the pump housing precursor at a temperature of at least 300° C.

16. The method of claim 15, wherein the forming of a pump housing precursor comprises a shaping process, selected from the group consisting of a lithographic process, an injection molding process, a machining process, an extrusion process or a combination of at least two thereof.

17. A pump housing for a pump device obtainable by a method as claimed claim 15.

18. A housing at least partly surrounding an interior region and comprising a first end and a second end;
wherein the housing has at least one first subregion and at least two further subregions, a material of the first subregion being different than a material of the two further subregions;
wherein the first subregion comprises a ceramic to an extent of at least 61% by weight, based on the total mass of the first subregion;
wherein the two further subregions comprises a metal content within a range from 40 to 90% by weight, based on the total mass of the two further subregions;
wherein at least one part of the first subregion and at least one part of the two further subregions are connected to one another; and
wherein the at least one further subregion is positioned at the first end or the second end of the interior region and wherein the at least one first subregion and the at least two further subregions alternate on an exterior circumference of the pump housing.

19. The housing of claim 18, wherein a slidable element is located in the housing, at least in one part of the housing.

* * * * *